United States Patent [19]

Weick

[11] Patent Number: 4,938,419

[45] Date of Patent: Jul. 3, 1990

[54] DEVICE FOR ATOMIZING OF ACTIVE SUBSTANCES

[76] Inventor: Heinz H. Weick, 94, Rue de la Servette, CH-1202 Geneve, Switzerland

[21] Appl. No.: 256,499

[22] Filed: Oct. 12, 1988

[30] Foreign Application Priority Data

Mar. 31, 1988 [CH] Switzerland .................. 1216/88
Aug. 9, 1988 [WO] World Int. Prop. O. .......... 8800134

[51] Int. Cl.$^5$ ................................................ A61L 9/12
[52] U.S. Cl. ...................................... 239/55; 239/58
[58] Field of Search ................................. 239/53-60; 220/8, 345, 352, 363, 364; 206/0.5

[56] References Cited

U.S. PATENT DOCUMENTS

| | | | |
|---|---|---|---|
| 2,878,060 | 3/1959 | Russo | 220/8 X |
| 2,959,354 | 11/1960 | Beck | 239/55 X |
| 3,575,346 | 4/1971 | Roth | 239/55 X |
| 3,908,906 | 9/1975 | Crowle et al. | 239/58 |
| 3,910,495 | 10/1975 | Cummings et al. | 239/58 |
| 3,946,945 | 3/1976 | Odiso et al. | 239/58 |
| 3,976,246 | 8/1976 | Hauri et al. | 239/57 |
| 4,352,457 | 10/1982 | Weick | 239/57 X |

Primary Examiner—Andres Kashnikow
Assistant Examiner—Kevin P. Weldon

Attorney, Agent, or Firm—Tarolli, Sundheim & Covell

[57] ABSTRACT

The devices serves for the atomizing of active substances of a paramedicinal of a cosmetic nature. It consists of a plate-form flat hollow body (1, 2) with two wide-side walls (1b, 1b') of which at least one has a zone designed porous, and with a slide-type cover element (5), arranged to be pushed along with sliding on the latter. To seal the device against loss of active substance, the hollow body is provided with a circumferential push-in sealing groove (2b), open toward the cover element, and widening toward the outside. The cover element is provided, for the purpose of its engagement with a rim section in this push-in sealing groove, in its closed position, on the outside of this rim section, with a tapering (5b), corresponding to the push-in sealing groove. Moreover, the outer surfaces of the hollow body, in the zone of the push-in sealing groove and the inner surface of the cover element, at least in the zone of its rim section, are designed to lie tightly together in the closed position. The device may be used, both for an active atomization, for example, of paramedicinal active substances (use as a mouth and nose inhaler), and also for a passive atomization, for example of perfume (as a perfume distributor, either in the pockets of garments or as a socket device).

7 Claims, 1 Drawing Sheet

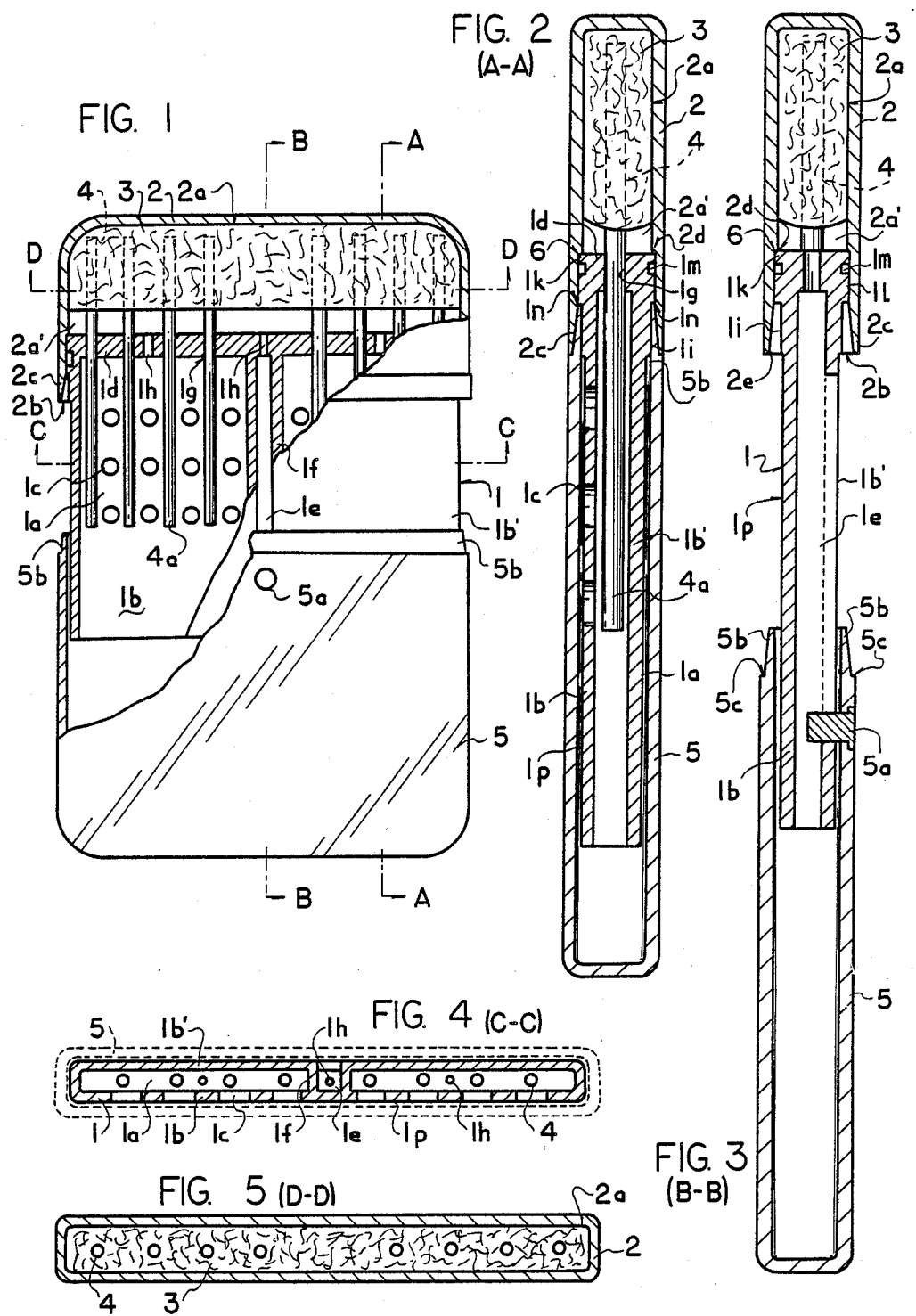

DEVICE FOR ATOMIZING OF ACTIVE SUBSTANCES

TECHNICAL FIELD

The invention relates to a device for the atomizing of active substances. It relates in particular to such a device having a plate-form flat hollow body with two wide-side walls, of which at least one has a porous zone, and a slide-type element which can be pushed along with sliding on the latter and which is movable from a closed position, covering the porous zone of the hollow body, into at least one atomizing position, freeing the zone at least partly.

Such a device serves for passive atomization (for example of perfume) as well as active atomization (for example of paramedical materials against catarrhal difficulties, to wean from smoking, or the like). For an active atomization, the device is held before the mouth or below the nose, in order to inhale the active substance through the porous atomizing zone.

Since the active substances are usually easily volatilized fluids, sometimes with very high vapor pressure, and between the manufacture of the device and its purchase by the final consumer there is often a great space of time, and the duration of use should be as long as possible, loss or sealing problems are of great importance. A perfect sealing is necessary, therefore, because the legislatures of many countries demand a product stability, which may be between 2 and 5 years, depending on the country. By stability is to be understood, in regard to atomizing devices of this kind, that the fluid inside the device does not change within the legally prescribed period of time, and thus cannot escape. If, for any reason, the prescribed time period cannot be guaranteed, the product must bear an expiration date, just as in foodstuffs.

STATE OF THE ART

Up to now, one construction of the device described has become known. With this, the problem of gas-tightness could not be satisfactorily solved. In particular, the cover element, in its closed position, does not close sufficiently gas-tight. Therefore, the sealing zone between the hollow body and the covering element has been surrounded by a self-sticking sealing band of aluminum foil, which is relatively expensive, and because of the flat form of the device is difficult to position. A sufficiently gas-tight gluing cannot be attained with a self-sticking band. To compensate the surface roughness of the hollow body and the covering element, a great deal of glue must be used, which after the removal of the sealing band on the device, leads to undesired residues. The improvement of sealing attained by the sealing band is given, moreover, only until the first use of the device by the consumer. The higher loss occurring then still shortens considerably the time of use. The high cost of the active substance makes this condition still more unsatisfactory and the customer has available only a part of the content for which he has paid.

REPRESENTATION OF THE INVENTION

The invention attacks, in particular, the problem, in a device of the kind mentioned, of increasing the sealing, with the simplest possible means. This and other problems are solved, according to the invention, by a device with the features of claim 1.

According to the invention, therefore, the hollow body is provided with a circumferential push-in sealing groove, open toward the cover element and widening outward, and the cover element, for the purpose of its engagement by a rim section, into this push-in sealing groove, in its closed position, is provided on the outside of this rim section, with a tapering corresponding to the push-in sealing groove. Also, at least the outer surfaces of the hollow body in the zone of the push-in sealing groove, and at least the inner surfaces of the sealing element, in the zone of its rim section, are designed as smooth sealing surfaces, lying close together in the closing position.

If the cover element, sliding on the hollow body, is pushed into its closed position, this tapered rim section arrives in the push-in sealing groove. Since it is tapered inward, the rim section, from a certain push-in position, can only be pushed farther into the push-in sealing groove under elastic deformation of itself and mainly of this latter. With this, the sealing surfaces on the hollow body and on the sealing element are pressed together elastically, by which an excellent sealing effect is given.

According to one preferred embodiment of the invention, the hollow body in the zone of the push-in sealing groove and its sealing surfaces arranged therein, are slightly reinforced, circumferentially, so that the sealing surface is somewhat raised, at least opposite the porous zone of the hollow body. In pushing the cover element, by its rim zone, into the push-in sealing groove, this rim zone travels onto the slightly raised sealing surface. The raising of the sealing surface effects, advantageously, a certain increase of the elastic tension, by which the sealing surface on the hollow body, in the zone of the push-in sealing groove, and on the cover element, at its rim section, are pressed together, in the closed position, and it is also assured that these surfaces will lie perfectly against each other everywhere. It is further achieved through this raising that the cover element can be designed easily accessible and movable above the rest, especially the zone of the hollow body which is designed porous.

Another preferred embodiment of the invention lies in the fact that at least the wide-side wall of the hollow body, designed porous and the wall of the cover element, sliding on the latter, are held at a distance by tiny distance slide ridges, which have less height than the sealing surface on the hollow body is raised at least opposite its porous zone. These distance slide ridges prevent drops of active material (getting between the cover element and the wide-side wall, by way of condensation, for example) from being able to lead to a wetting of the surface as a result of the moving of the cover element.

According to another preferred embodiment of the invention, the hollow body is composed of a first and a second part, the second part gripping around the first part by an end section, and the push-in sealing groove being formed by an inside tapering on the said end section of the second part of the hollow body. With such a two-part design of the hollow body, preferably, its first and second parts are welded together in their overlapping zone by means of a circumferential welding seam. To produce the welding seam, it is further preferable that the first part of the hollow body be provided peripherally with a circumferential thin ridge of welding which engages a step-form hollow in the end section of the second part of the hollow body. The welding seam should be arranged not more distant from the push-in sealing groove than the depth of the latter. In particular, by such a positioning of the welding seam, a considerable reinforcement is given in the zone of the push-in sealing groove, which, by increasing the elastic tensions in the closed position of the cover element, has a further reinforcing effect on the hermetic quality.

The above-mentioned and further advantageous embodiments and further developments of the present invention are distinguished in the dependent claims.

BRIEF DESCRIPTION OF THE DRAWINGS

In the drawings are shown one example of execution of the invention, from the description of which the advantages attained through the invention, as well as the abovementioned preferred embodiments and further developments will appear clearly.

FIG. 1 a side view in partial section of the device;
FIG. 2 shows a section A—A according to FIG. 1;
FIG. 3 shows a section B—B according to FIG. 1;
FIG. 4 shows a section C—C according to FIG. 1; and
FIG. 5 shows a section D—D according to FIG. 1.

In the several figures, corresponding parts are given the same reference numbers.

To attain as great as possible a clarity on the individual details of construction, the figures have been represented on different scales. On the other hand, the device in the design for carrying in the pockets of garments is so dimensioned that it can fit, for example, even into a small chest pocket of a shirt or blouse. For a socket (pedestal, stand) device, the size is of less importance.

THE BEST WAY OF CARRYING OUT THE INVENTION

Let us now refer to the drawing. The plate-form flat hollow body 1, 2 represented therein consists of the first part 1, enclosing an atomizing chamber 1a (atomizing chamber part), and serving at the same time as a handle part, and the second part 2, containing the reserve chamber 2a of active substance (reserve chamber part). These two parts are fastened together by a circumferential ultrasonic welding. The reserve chamber 2a is filled, up to the narrow free space 2a', by a socket form enclosed tampon 3 of absorptive material. The atomizing chamber 1a and the reserve chamber 2a are separated from each other by a transverse wall 1d which is formed on the first part 1, projecting into the second part 2. In the transvese wall 1d are provided passage channels 1g through which lead wick-type conductors 4 of active substance extend. The wick-type conductors 4 of active substance project, by their upper lengthwise zones, in FIGS. 1 to 3, into the tampon 3. By their lower zones 4a in the Figures, they extend into the atomizing chamber 1a, and there take up the atomizing function directly. They are essentially form-stable, straight-line design, and preferably consist of chemical fibers.

In the transverse wall 1d are also pressure-compensating openings 1h, which also serve to replenish the reserve chamber 2a by means of injection canules (small tubes). One, 1b, of the two wide-side walls 1b, 1b' of the atomizing chamber part 1 is provided with atomizing holes 1c, arranged in rows, and is thus designed porous. The cover element 5 is designed as a slide-type body, enclosing closely the atomizing chamber part 1 of the hollow body 1, 2, and sliding on this latter. It has inside, to limit maximum pull-out position, a centrally arranged cylindrical stop cam 5a, which engages in a lengthwise stop groove 1e of the atomizing chamber part 1. This groove is limited on both sides by stays 1f and has no connection to the atomizing chamber 1a.

The lengthwise zones 4a of the active substance conductors 4 have a certain distance from the side walls 1b, 1b' of the part 1 of the atomizing chamber. In this way, an undesired wetting of the walls is prevented. So that the active substance conductors 4 will remain in this position, they are, as already mentioned, designed essentially form-stable and straight-line and are arranged, in each case, protected between the lengthwise rows of atomizing holes 1c. Moreover, the stays 1f of the atomizing chamber part 1 secure the mutual distance of the walls 1b, 1b'. It is not absolutely necessary, however that the active substance conductors have absolutely no contact with the side walls. With a preferred distance of only some 1/10 mm, a certain mutual contact, for example, even because of a slight bending of the active substance conductors, cannot always be completely prevented. But such a contact has no harmful consequences, and is tolerable, at least when it is, more or less, only at a certain point.

The transition zone between the atomizing chamber part 1 and the reserve chamber part 2, as well as that between the hollow bodies 1, 2 and cover element 5, in the cooperating sealing zones of their closed position, have a very special new kind of design. Thus, first of all, the reserve chamber part 2, in the zone of its end section, gripping around the atomizing chamber part 1, has, for the formation of a circumferential push-in sealing groove 2b, open toward the cover element 5, and widening toward the outside, the inside conical tapering 2c. For the purpose of engagement in this, the rim section or opening zone of the cover element 5 is provided outside with the corresponding conical tapering 5b.

The outer surface of the atomizing chamber part, in the zone of the push-in sealing groove, and the inner surface of the cover element, at least in the zone of its rim section, are designed as smooth sealing surfaces. In the closed position (FIG. 2), the sealing surfaces lie tightly together. The depth of roughness of the sealing surfaces is between about 2/1000 mm and about 3/1000 mm. Moreover, the wall thickness of the atomizing chamber part 1, in the zone 1i of the push-in sealing groove 2b1, and with this, the sealing surface around it is slightly reinforced, preferably by a few tenths of a millimeter.

The conically tapered surfaces 2c and 5b are also designed as correspondingly smooth sealing surfaces.

To the tapered rim zone 5b of the cover element 5 is adjoined an offset 5c, springing outward, which, in the closed position of the cover element, when its said rim zone engages in the push-in sealing groove 2b, lies against the opening rim 2e of the push-in sealing groove. The offset 5c is so arranged that the cover element, by its rim section, to reach the closed position, must be pressed somewhat into the push-in sealing groove, with a certain elastic deformation of same. The depth of the push-in sealing groove 2b is so dimensioned that, in this position, there still remains in its rear zone a small circumferential hollow space.

The circumferential ultrasonic welding is marked 6. It is distanced from the push-in sealing groove by not more than the depth of same. This gives a desired high stiffness of the reserve chamber part 2 in the zone of the push-in sealing groove 2b. To produce the weld seam, there is formed on the atomizing chamber part 1, around its peripheral side, a circumferential thin weld ridge 1k. This lies against the step-form hollow 2d of the reserve chamber part 2. These special construction measures of welding technology allow a perfectly gas-tight welding, although it must be carried out with very low welding energy to prevent a deformation of the atomizing chamber 1, which is very thin-walled and weakened by the atomizing holes. Because of the arrangement and slight thickness of the welding ridge 1k, an ideal, oscillate, potential is effective in the welding contact zone, by which the weld ridge 1k presses resiliently against the offset 2d, and joins gas-tight with the latter with simultaneous deformation.

Between the welding 6 and the push-in sealing groove 2b, there is still another narrow, circumferential groove, caused by the forming of the weld ridge 1k and another ridge 11.

The sealing conditions attained are as follows:

When the cover element 5, sliding easily on the atomizing chamber part 1, is pushed into its closed position, its tapered rim section or opening zone 5b arrives in the push-in sealing groove 2b while, at the same time, it moves onto the reinforced zone 1i of the atomizing chamber part 1. Since the walls of the reserve chamber part 2, because of the welding 6 and their position give out only slightly, that is only the desired amounts, the rim section of the cover element 5 is clamped in the push-in sealing groove, in which a small hollow space still remains. The opening rim 2e of the reserve chamber part serves as stop for the cover element 5.

From the atomizing chamber out, therefore, for the active substance atomized in the latter, two sealing surfaces exist, one arranged after the other. An inner sealing surface between the reinforced wall zone 1i and the inner surface of the rim section of the cover element 5, and an outer sealing surface between the tapering 5b and the tapering 2c compared with each other, the inner sealing surface, as a rule, has a clearly better and also more secure sealing effect than the outer sealing surface. If condensed fluid arrives in the zone of the inner sealing surface, this can penetrate, as a result of capillary action, only into the hollow space interrupting the effect. Therefore, the sealing is practically perfect, even as to a wetting of the inner sealing zone with condensed active substance.

Through the gas-tight welding 6, a loss from the reserve chamber 2a of fluid or even already-gasified active substance is excluded. But should such a welding not be perfect, the necessary sealing is still given, to a sufficient degree, by the groove 1m, interrupting capillary action, and the outer sealing surface, lying in series with this, between the two taperings 2c and 5b.

It also appears, especially from FIGS. 2 to 4, that on the outside of the wide-side wall 1b, between the lengthwise rows of atomizing holes 1c, tiny distance slide ridges 1p are also provided. These prevent drops of active substance, getting between the cover element 5 and the side wall 1b, by condensation, for example, as a result of the movement of the cover element 5, from leading to a wetting of the surface. Although such a wetting can occur mainly on the side of the atomizing holes, corresponding ridges may of course be formed on the outside of the side wall 1b'. As an alternative, such ridges might be on the inner surface of the cover element 5. It is important that the distance slide ridges have less height, (about 1/10 to 2/10 mm) than the sealing surface in the reinforced wall zone 1i on the hollow body is raised, at least opposite at least its porous zone, so that the effect of this reinforcement is retained.

In the device described, only the wide-side wall 1b of the atomizing chamber part 1 is provided with atomizing holes 1c. So designed, this device serves preferably as a mouth and nose inhaler (for example, for the atomizing of an active substance for clearing the breathing passages, or with a healing effect, such as eucalyptus oil, in inflammatory diseases of the breathing passages, or an active substance for clearing smoke from the dwelling, or the like). For inhaling, the device is held, by its side containing the atomizing holes 1c, directly against the mouth or beneath the nose. During inhalation, outside air penetrates through the atomizing holes not covered by the mouth or nose, into the atomizing space 1a, flows parallel to the wide-side walls 1b, 1b', past the zone 4a of the active substance conductors, and arrives (intensively enriched with active substance) into the corresponding breathing passages.

If the device is to be used for the atomizing of perfume, naturally, the atomizing effect is greatest when both wide-side walls 1b, 1b' are provided with atomizing holes 1c, since in this use, the air does not necessarily flow through the atomization chamber 1a. The device is suitable as a perfume atomizer by means of a separate or molded socket (the reserve chamber might be in the socket zone), or by means of a support base to be placed on the desk or the like. As a socket device, the device may naturally be larger than when it is intended to be carried along in the pocket of a garment.

I claim:

1. A device for the atomizing of active substances, said device comprising:
   a plate-form flat hollow body including two wide-side walls of which at least one wide-side wall has a porous zone;
   a slide-type cover element slidably movable on the hollow body, the cover element being adjustable from a closed position which covers the porous zone of the hollow body to at least one atomizing position which at least partially frees the porous zone;
   the hollow body (1, 2) defining a circumferentially push-in sealing groove (2b) which is open toward the cover element (5) and which widens toward the outside, the cover element including a tapered rim portion (5b) located on the outside of the cover element for engaging with the hollow body in the push-in sealing groove when the cover element is in the closed position; and
   at least the outer surface of the hollow body at the push-in sealing groove and at least the inner surface of the cover element at the tapered rim portion being smooth sealing surfaces and lying tightly against each other when the cover element is in the closed position, the hollow body at the push-in sealing groove and its sealing surface being slightly reinforced circumferentially so that the outer surface of the hollow body at the push-in sealing groove is at least raised relative to the porous zone of the hollow body.

2. A device as set forth in claim 1 wherein the hollow body (1, 2) includes a first part (1) and a second part (2) having an end portion gripping around the first part (1) to form an overlapping portion of the first and second parts, the push-in sealing groove (2b) being formed by an inside tapering (2c) on the end portion of the second part of the hollow body, the first and second parts of the hollow body being welded together at the overlapping portion by a circumferential welding seam (6), the first part of the hollow body being provided peripherally with a circumferential thin ride of welding (1*k*) which engages in a step-form offset (2*d*) in the end portion of the second part of the hollow body.

3. A device as set forth in claim 1 wherein the at least one wide-side wall having the porous zone and a wall of the cover element are held at a distance by distanced slide rides (1*p*).

4. A device as set forth in claim 3 wherein the distance slide ridges (1*p*) are less high than the sealing surfaces of the hollow body at least opposite the porous zone of the hollow body.

5. A device for the atomizing of active substances, said device comprising:

a plate-form flat hollow body including two wide-side walls of which at least one wide-side wall has a porous zone;

a slide-type cover element slidably movable on the hollow body, the cover element being adjustable from a closed position which covers the porous zone of the hollow body to at least one atomizing position which at least partially frees the porous zone;

the hollow body (1, 2) defining a circumferentially push-in sealing groove (2*b*) which is open toward the cover element (5) and which widens toward the outside, the cover element including a tapered rim portion (5*b*) located on the outside of the cover element for engaging with the hollow body in the push-in sealing groove when the cover element is in the closed position; and at least the outer surface of the hollow body at the push-in sealing groove and at least the inner surface of the cover element at the tapered rim portion being smooth sealing surfaces and lying tightly against each other when the cover element is in the closed position, the hollow body at the push-in sealing groove and its sealing surface being slightly reinforced circumferentially so that the outer surface of the hollow body at the push-in sealing groove is at least raised relative to the porous zone of the hollow body, the at least one wide-side wall having the porous zone and a wall of the cover element being held at a distance by distanced slide ridges (1*p*).

6. A device as set forth in claim 6 wherein the hollow body (1, 2) includes a first part (1) and a second part (2) having an end portion gripping around the first part (1) to form an overlapping portion of the first and second parts, the push-in sealing groove (2*b*) being formed by an inside tapering (2*c*) on the end portion of the second part of the hollow body, the first and second parts of the hollow body being welded together at the overlapping portion by a circumferential welding seam (6), the first part of the hollow body being provided peripherally with a circumferential thin ridge of welding (1*k*) which engages in a step-form offset (2*d*) in the end portion of the second part of the hollow body.

7. A device as set forth in claim 6 wherein the distance slide ridges (1*p*) are less high than the sealing surfaces of the hollow body at least opposite the porous zone of the hollow body.

* * * * *

UNITED STATES PATENT AND TRADEMARK OFFICE
CERTIFICATE OF CORRECTION

PATENT NO. : 4,938,419

DATED : July 3, 1990

INVENTOR(S) : Heinz H. Weick

It is certified that error appears in the above-identified patent and that said Letters Patent is hereby corrected as shown below:

Column 8, Line 15, Claim 6, change "6" to --5--.

Signed and Sealed this

Twenty-fourth Day of September, 1991

Attest:

HARRY F. MANBECK, JR.

Attesting Officer

Commissioner of Patents and Trademarks